United States Patent [19]

Pennella

[11] 4,414,083

[45] Nov. 8, 1983

[54] REMOVAL OF DIENE IMPURITIES FROM ALKENES OR ALKANES OVER ACTIVATED MAGNESIUM OXIDE UNDER ULTRAVIOLET RADIATION

[75] Inventor: Filippo Pennella, Bartlesville, Okla.

[73] Assignee: Phillips Petroleum Company, Bartlesville, Okla.

[21] Appl. No.: 343,047

[22] Filed: Jan. 27, 1982

[51] Int. Cl.$^3$ .............................................. C07C 3/24
[52] U.S. Cl. .............................................. 204/162 R
[58] Field of Search .................. 204/162 R; 585/700, 585/702, 744, 750

[56] References Cited

U.S. PATENT DOCUMENTS

| | | | |
|---|---|---|---|
| 3,574,076 | 4/1971 | Kirsch | 204/162 R |
| 3,838,926 | 10/1974 | Kato | 356/208 |
| 4,036,904 | 7/1977 | Strope | 260/681.5 R |
| 4,287,378 | 9/1981 | Pennella | 585/643 |

*Primary Examiner*—Benjamin R. Padgett
*Assistant Examiner*—M. Moskowitz

[57] ABSTRACT

Dienes such as 1,3-butadiene, in relatively low concentration, are removed from mono-olefins, such as propylene and normal butenes, by passage over a catalyst of activated magnesium oxide while irradiated with ultraviolet light.

9 Claims, No Drawings

REMOVAL OF DIENE IMPURITIES FROM ALKENES OR ALKANES OVER ACTIVATED MAGNESIUM OXIDE UNDER ULTRAVIOLET RADIATION

This invention relates to the removal of alkadiene impurities from a gaseous stream of hydrocarbons comprising alkanes and alenes, where a gas stream essentially free of such impurities is desired. In many industrial chemical processes it is desirable to provide hydrocarbon feed streams which are essentially pure, as for certain polymerization reactions, or at least essentially free of certain impurities which might poison catalysts or otherwise interfere with the process reaction or other uses of such feed streams. For instance, U.S. Pat. No. 4,036,904 discloses a process for reducing the amount of allenic impurities in a $C_4$ feedstream, which comprises contacting the $C_4$ stream with magnesium oxide, whereby the allenic impurities in the stream are converted to compounds which do not adversely affect the catalysts or catalyst systems subsequently employed.

Since such impurities may be present in such small quantities and/or are so similar to the feedstream that ordinary treatment, such as fractional distillation, may not be feasible for their removal, other methods may be necessary to reduce the amount of such impurities to acceptable levels for certain applications of the feedstream. Particularly where polymerization reactions and/or catalytic reactions are involved, such impurities should preferably be reduced to a level as low as practicable.

SUMMARY OF THE INVENTION

It is an object of this invention to provide a process to remove, or reduce the amount of, dienes in a gaseous stream of alkenes and/or alkanes. A particular object is to reduce the content of conjugated alkadienes comprising 1,3-butadiene to a very low level in streams of alkenes and/or alkanes having a number of carbon atoms the same as, or only one carbon atom more or less than, such impurities, e.g., propylene, butenes and pentenes.

Other objects, aspects and advantages of the present invention will be apparent to those skilled in the art from a reading of the following disclosure and the appended claims.

In accordance with the present invention there is provided a process for removing, or reducing the amount of, dienes having up to five carbon atoms from a gaseous hydrocarbon stream of alkanes and/or alkenes containing up to five carbon atoms, which comprises contacting such hydrocarbon stream with magnesium oxide, while irradiating said stream and magnesium oxide with ultraviolet light. The diene impurities are thus removed from the stream and/or converted to compounds which, e.g., do not adversely affect the catalysts, catalyst systems, or reactions to be subsequently employed.

More specifically, the diene impurities which can be removed or converted in accordance with the present invention include 1,3-butadiene, which has the formula

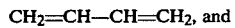

$CH_2=CH-CH=CH_2$, and other conjugated or unconjugated dienes having up to five carbon atoms, comprising propadiene, 1,2-butadiene, pentadiene, and isoprene.

The present invention can be used to remove dienes which are present as minor impurities in gaseous streams of alkenes and/or alkanes, i.e., less than about 1 weight percent, preferably less than 0.1 weight percent. A preferred stream for such purification is a butene, or mixture of butenes.

The diene impurities are removed by contacting the stream containing such impurities with a magnesium oxide catalyst at a temperature of from ambient to about 300° C., preferably 20° C.–200° C., under irradiation by ultraviolet light, at a rate of about 100 to 5000, preferably about 200 to 1000, volumes of gas per volume of catalyst per hour.

To optimize the contacting of the hydrocarbons and catalyst under the ultraviolet irradiation, a moving bed, such as a fluidized or ebullating bed, is preferred. The process is preferably carried out in the gas phase. Pressures ranging from about atmospheric to less than the vapor pressure of the hydrocarbon at the process temperature can be used. Thus, where the stream is a mixture of hydrocarbons, the partial pressure of each hydrocarbon, including the diene impurities, should be less than its vapor pressure at the process temperature, so as to maintain the system in the gas phase.

Ultraviolet light such as emitted from a low-pressure high-intensity mercury vapor lamp can be used, subjecting the hydrocarbon stream and catalyst to ultraviolet light of a wavelength preferably ranging from about 2000 to 3000 Angstroms. The ultraviolet light can be introduced to the reactor through a transparent window or reactor wall, or other means, e.g., a lamp inside the reactor, such that the reactor walls form an annulus about the lamp surface.

The catalyst of this invention is magnesium oxide. In one embodiment, the magnesium oxide can be obtained by heating a compound containing magnesium, such as magnesium hydroxide, which decomposes to produce magnesium oxide. Minor amounts of other materials, such as silicon oxide or aluminum oxide, can be present as impurities without departing from the scope of the invention. Depending upon the contacting technique to be used in this invention, the magnesium oxide can be in the form of pellets, extrudates, or fine powder. The magnesium oxide is activated by heating in air, preferably in a stream of flowing air, from 0.1 to 10 hours, or longer, at a temperature of 200° to 800° C., preferably about 400° to 600° C.

The ultraviolet radiation to the reaction zone can be supplied by commercially available photochemical mercury arc lamps, such as those sold by General Electric and Ultraviolet Products, Inc. The lamps are placed in the vicinity of the reactor in the manner conventionally employed in the art, with the output of the lamps sufficient to provide a suitable illumination intensity throughout the moving catalyst bed. Medium pressure mercury arc lamps are exemplary of suitable lamps operable in the instant invention. The radiation generated from such lamps typically has wavelengths of 2537, 3130, 3650, 4047, 4358, 5461 and 5780 Angstroms. Since ultraviolet radiation is considered to be in the range of about 1000 to 4000 Angstrom units, then the first three wavelengths mentioned will produce ultraviolet radiation which has been found particularly useful. However, radiation above 4000 Angstroms can be utilized. Low pressure lamps suitable for the practice of the present invention are characterized by relatively little heat evolution during operation and almost exclusive generation of the 2537 Angstrom spectral line. Other suitable lamps include hot cathode (germicidal lamps)

and cool cathode (sterilamps) which provide sources of the 2537 Angstrom spectral line. It has been found that the effect of the electromagnetic radiation is not one of supplying heat, but is simply that of light radiation.

The specific reaction conditions of temperature, pressure, flow rates, form of catalyst, intensity of ultraviolet irradiation, etc. for optimum removal of impurities will vary with the hydrocarbon stream and particular diene impurities involved. For example, the reaction is preferably carried out at a pressure less than the vapor pressure of the hydrocarbon stream at the process temperature, to keep the stream in the gas phase. To obtain the required contact time of the impurities with the catalyst under ultraviolet irradiation will normally require regulation of the space velocity to suit the apparatus and process. Lower temperatures are generally preferred for removing impurities from hydrocarbons which are more subject to double bond isomerization at higher temperatures, such as 1- and 2-butene. The configuration and output of the ultraviolet lamps should be such that the intensity of the radiation is sufficient and suitable for the inventive process throughout the moving bed of catalyst.

The following example will specifically demonstrate the practice of the present invention and its advantages. It is to be understood that this example is utilized merely for illustrative purposes, and should not be considered as limiting the invention.

EXAMPLE

Use of ultraviolet radiation to remove 1,3-butadiene from propylene over magnesium oxide has been demonstrated as follows. Runs were made using one gram of $-20+40$ mesh MgO that was placed in a 7 mm i.d. quartz tube, making an 8 cm column of solid. The quartz reactor had a thermowell permitting the temperature of the MgO to be measured with a thermocouple. Surrounding the quartz reactor was a heater consisting of two concentric quartz tubes having a resistance wire heater wrapped on the outer surface of the inner tube. Ultraviolet radiation was provided from three (sometimes four) nearly circular UV lamps that surrounded the reactor-heater assembly.

The lamps used were low-pressure mercury vapor lamps, model PCOX1, from Ultraviolet Products, Inc. Four independently operable lamps were arranged to define a cylinder, approximately 3 inches in diameter and 5 inches long, surrounding the reactor-heater assembly. The resulting unit drew approximately 75 watts and produced an intensity of 2537 Angstrom radiation at the axis of the cylinder of about 30 milliwatts per cm$^2$.

Propylene feed rate was measured on reactor effluent with a soap film buret. Gas samples were analyzed by GLC having a flame ionization detector; analyses for butadiene are sensitive to less than one ppm (0.0001%).

Before testing this invention the MgO was treated with flowing air for one hour at 600° C., flushed with dry nitrogen for 15 min. at 500° C., then cooled under nitrogen. Table I shows that irradiation with ultraviolet light is effective to completely remove the butadiene from the feedstream. The temperature of the MgO is raised somewhat by the heat emitted by the UV lamps.

TABLE I

| Run No. | UV light On | Temp., °C. | $C_3H_6$ rate mL/m | Gas Composition, Volume Percent | | | | | | |
|---|---|---|---|---|---|---|---|---|---|---|
| | | | | $C_2H_4$ | $C_3H_8$ | $C_3H_6$ | 1-$C_4H_8$ | trans-2-$C_4H_8$ | cis-2-$C_4H_8$ | 1,3-$C_4H_6$ |
| FEED | | | | 0.007 | 0.658 | 99.3 | 0.03 | 0.01 | 0.003 | 0.004 |
| 1 | No | 25 | 20 | 0.007 | 0.658 | 99.3 | 0.03 | 0.01 | 0.003 | 0.004 |
| 2 | Yes | 36 | 20 | 0.013 | 0.668 | 99.3 | 0.03 | 0.02 | 0.009 | Nil |
| 3 | Yes | 36 | 2 | 0.05 | 0.63 | 99.2 | 0.009 | 0.068 | 0.031 | Nil |
| 4 | No | 30 | 2 | 0.008 | 0.665 | 99.3 | 0.029 | 0.011 | 0.003 | 0.004 |
| 5 | Yes | 40 | 3 | 0.026 | 0.62 | 99.3 | 0.012 | 0.035 | 0.015 | Nil |

TABLE II

| Run | UV light on | Temp., °C. | $C_3H_6$ rate, mL/min. | $C_4H_6$, % |
|---|---|---|---|---|
| 6 | Yes | 400 | 22 | 0.004 |
| 7 | Yes | 300 | 22 | 0.002 |
| 8 | Yes | 200 | 22 | Nil |
| 9 | Yes | 150 | 22 | Nil |
| 10 | Yes | 150 | 60 | 0.001 |
| 11 | Yes | 130 | 60 | 0.001 |
| 12 | Yes | 90 | 60 | 0.001 |
| 13 | Yes | 70 | 60 | 0.001 |
| 14 | Yes | 60 | 20 | Nil |

A separate series of runs demonstrated that the effectiveness of the method of this invention is diminished by elevated temperature. The magnesium oxide was activated as described in the preceding paragraph. After cooling to 50° C. the feed used previously was started at 22 mL/min. No change in 1,3-butadiene concentration occurred. The temperature was then increased in 50° C. increments of 50° C. to 400° C. Product samples were analyzed at each temperature; all samples contained 0.004% butadiene. At that temperature the UV lights were turned on and the runs recorded in Table II were made. It is seen that the method loses effectiveness at temperatures above 200° C. It is also seen to be sensitive to residence time; an approximate three-fold increase in feed rate permitted some butadiene to escape removal.

I claim:

1. A process for reducing the amount of diene impurities in a gaseous stream of hydrocarbons comprising alkanes and/or alkenes having up to five carbon atoms and at least one diene impurity, which process comprises contacting said stream with an activated magnesium oxide catalyst at a temperature in the approximate range of about 20° C. to about 300° C., and under ultraviolet light radiation.

2. A process in accordance with claim 1, wherein said diene impurities comprise dienes having up to 5 carbon atoms.

3. A process in accordance with claim 2, wherein said diene impurity is 1,3-butadiene.

4. A process in accordance with claim 1, wherein said contacting is carried out at pressures ranging from about atmospheric to pressures such that the partial pressures of said hydrocarbons are less than their vapor pressures at the process temperature.

5. A process in accordance with claim 1, wherein said ultraviolet light has a wavelength in the approximate range of 2000 to 3000 Angstroms, and is provided by lamps whose arrangement and output are sufficient to provide a suitable illumination intensity throughout said catalyst.

6. A process in accordance with claim 1, wherein said stream of hydrocarbons is contacted with said catalyst, in the presence of said ultraviolet light, at a temperature in the range of about 20° C. to about 200° C.

7. A process in accordance with claim 6, wherein said catalyst forms a moving, fluidized or ebullating bed.

8. A process in accordance with claim 1, wherein said stream of hydrocarbons is contacted with said catalyst at a suitable rate, ranging from about 100 to about 5000 volumes of gas per volume of catalyst per hour.

9. A process in accordance with one of claims 1, 2 or 3, wherein the concentration of said diene impurity is reduced to less than one part per million.

* * * * *